US00PP26499P3

(12) United States Plant Patent
Mazzardis

(10) Patent No.: US PP26,499 P3
(45) Date of Patent: Mar. 15, 2016

(54) PEACH TREE NAMED 'ALPINE DELIGHT'

(50) Latin Name: *Prunus persica*
Varietal Denomination: Alpine Delight

(71) Applicant: Vincent Mazzardis, Joondalup (AU)

(72) Inventor: Vincent Mazzardis, Joondalup (AU)

(73) Assignee: OZ PEACH PTY. LTD., Toowoomba (AU)

( * ) Notice: Subject to any disclaimer, the term of this patent is extended or adjusted under 35 U.S.C. 154(b) by 100 days.

(21) Appl. No.: 14/120,854

(22) Filed: Jul. 2, 2014

(65) Prior Publication Data

US 2015/0113689 P1 Apr. 23, 2015

(30) Foreign Application Priority Data

May 2, 2013 (ZA) ..... 6941

(51) Int. Cl.
*A01H 5/08* (2006.01)

(52) U.S. Cl.
USPC ..... Plt./195

(58) Field of Classification Search
USPC ..... Plt./195
See application file for complete search history.

(56) References Cited

FOREIGN PATENT DOCUMENTS

ZA PVJ 138 4/2013

*Primary Examiner* — Susan McCormick Ewoldt
(74) *Attorney, Agent, or Firm* — Randall Danskin

(57) ABSTRACT

A new peach tree variety is described and which is denominated varietally as 'Alpine Delight', and wherein the new peach tree variety produces fruit which are ripe for harvesting and shipment about October 2-15 under the ecological conditions prevailing near Perth, Australia.

3 Drawing Sheets

Latin name: *Prunus persica.*
Varietal denomination: Alpine Delight.

BACKGROUND OF THE NEW VARIETY

The present invention relates to a new, novel, and distinct variety of peach tree, *Prunus persica*, and which has been denominated varietally as 'Alpine Delight.' The present variety of peach tree resulted from an on-going program of fruit breeding. The purpose of this program is to improve the commercial quality of low chill peach and nectarine varieties, by creating and releasing promising selections of *Prunus* species. To this end, I make both controlled and hybrid cross pollinations each year in order to produce seedling populations from which improved progenies are evaluated and selected.

The seedling, 'Alpine Delight' was originated by me, and selected from a population of seedlings growing in my experimental orchard, and which is located near Perth, Western Australia. The seedlings, grown on their own roots, were derived from a cross that I made in 2008 of the white-fleshed, nectarine 4-1WN (unpatented), and the white fleshed peach 3-3WP (unpatented), and which is an early season, white fleshed, non-melting, clingstone peach, and which was the seed parent. As the fruit ripened the resulting seed from, this cross was stratified, germinated, and then was subsequently grown in a greenhouse to an appropriate development stage. Subsequently, the new plants were field planted and then grown for further evaluation. One seedling, which is the present variety, exhibited especially desirable characteristics, and was then designated as 'YT-5.' This seedling was marked for subsequent observation. After the 2011 fruiting season, the newly identified variety of peach tree designated as 'YT-5,' was formally named 'Alpine Delight.' The new variety was then selected for advanced evaluation and re-propagation.

ASEXUAL REPRODUCTION

Asexual reproduction of this new and distinct variety of peach tree was accomplished by budding the new peach tree onto 'Coastguard' rootstock (un-patented). This was performed by me in my experimental orchard which is located near Perth, Western Australia. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Alpine Delight' is a new and distinct variety of peach tree, which is considered of large size, and which has a vigorous growth characteristic. This new peach tree is also a regular and productive bearer of relatively large, firm, white fleshed, clingstone fruit which has a good flavor and eating qualities. This new peach tree has a very low chilling requirement of approximately 100 hours, and further produces relatively uniformly sized fruit throughout the canopy of the tree. In addition to the foregoing, the fruit of the new peach tree also appears to have good handling and shipping qualities.

The 'Alpine Delight' peach tree bears fruit which are ripe for commercial harvesting on approximately October 1 to October 15 under the ecological conditions prevailing near Perth, Western Australia. The fruit of the subject variety exhibits a larger fruit size than the pollen parent 4-1WN (unpatented); and further has a slightly smaller but more highly colored fruit than the seed parent 3-3 WP (unpatented). The new variety ripens approximately 15 days earlier than the seed parent at the same geographical location.

BRIEF DESCRIPTION OF THE DRAWINGS

The accompanying drawings, which are provided, are color photographs of the new peach variety.

Figure 1:
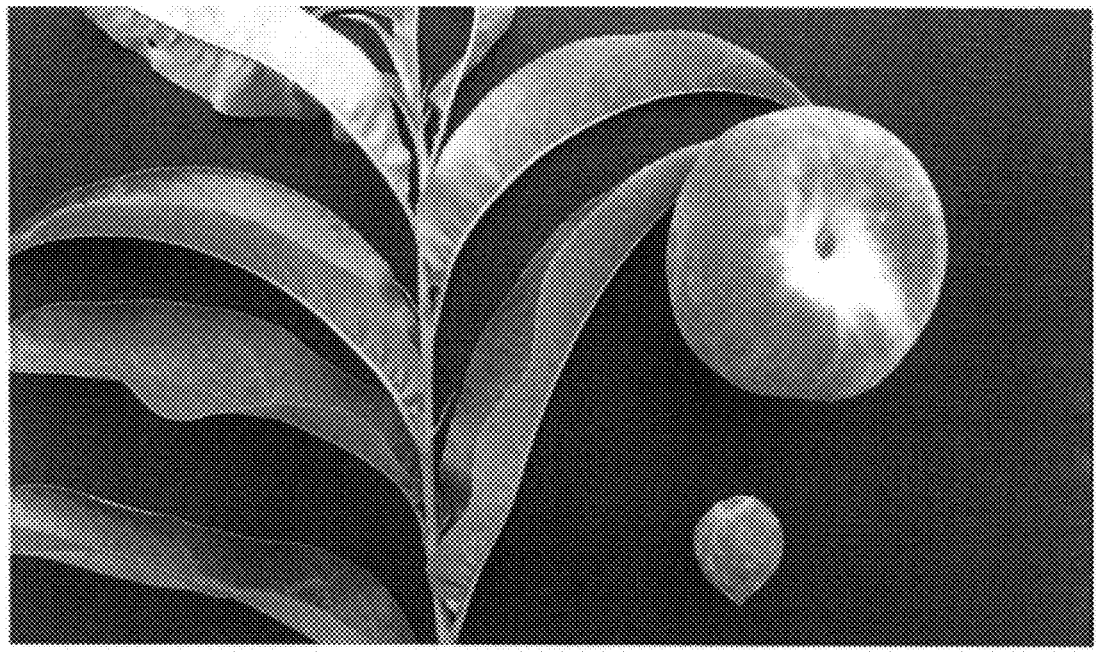
FIG. 1 depicts a whole mature fruit, which is sufficiently mature for harvesting and shipment; a twig bearing typical leaves, and a mature stone derived from a mature fruit.
Figure 2:
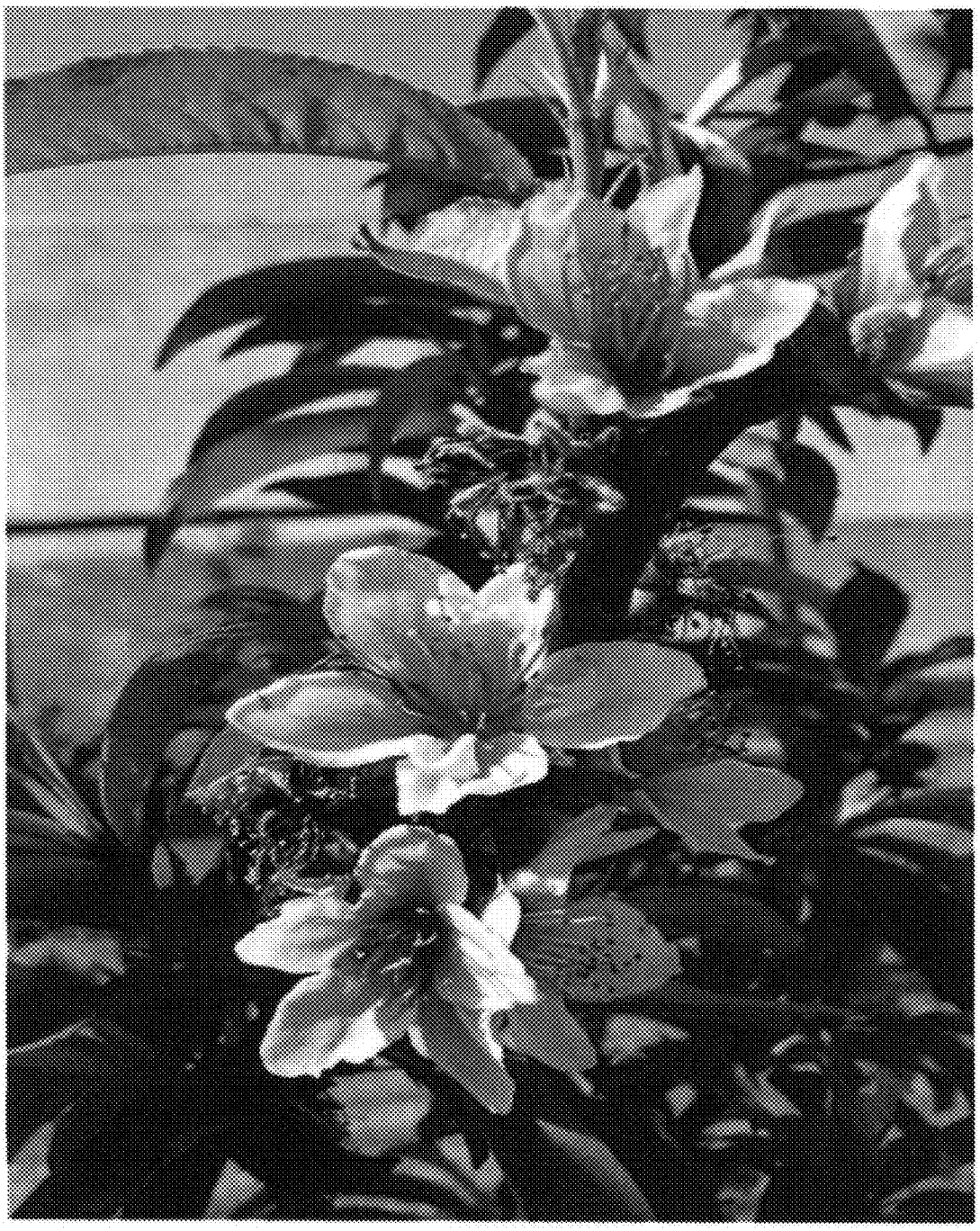
FIG. 2 depicts the flowering characteristics of the new, and novel variety of peach tree.
Figure 3:
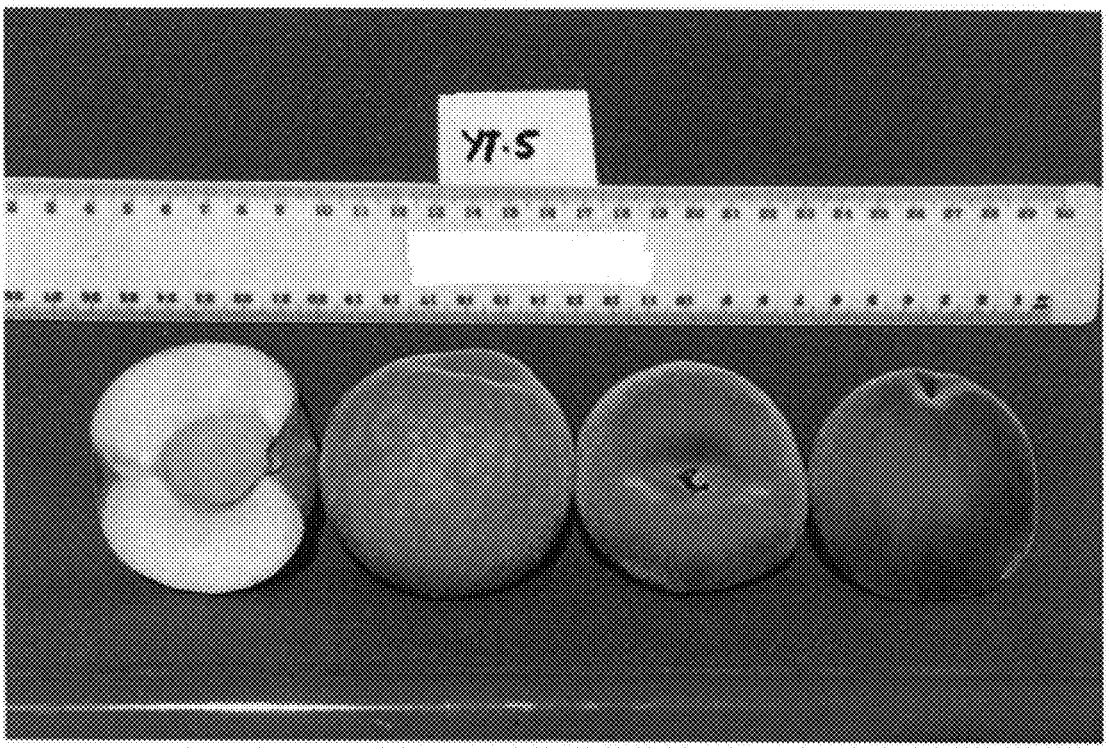
FIG. 3 depicts several mature fruit of the present variety, and which are positioned in various orientations so as to show the shape, and size of the mature fruit; and one mature fruit has been dissected longitudinally so as to display the flesh coloration and stone characteristics thereof.

The colors in theses photographs are as nearly true as is reasonably possible in a color representation of this type. Due to chemical development, processing and printing, the leaves and fruit depicted in these photographs may, or may not be accurate when compared to the actual specimen. For this reason, future color references should be made be made to the color plates (Royal Horticultural Society) and descriptions which are provided, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the third fruiting season under the ecological conditions prevailing at the orchard of the inventor, and which is located near the city of Perth, Western Australia. All major color code designations are by reference to The R.H.S. Colour Chart (Fifth Edition), and which is provided by The Royal Horticultural Society of Great Britain. Common color names are also occasionally used.

TREE

*Size*.—Generally — Considered large as compared to other commercial peach cultivars ripening in the early season of maturity. The tree of the present variety was pruned to a height of approximately 270 cm to about 310 cm at commercial maturity.

*Vigor*.—Considered vigorous. The present peach tree variety grew to about 300 cm in height during the first growing season. The new variety was pruned to a height of approximately 200 cm during the first dormant season.

*Productivity*.—Very productive. Fruit set varies from more than the desired crop load to levels much higher than the desired levels when grown in a suitable horticultural zone, and under appropriate commercial conditions. The fruit set is spaced by thinning to develop the remaining fruit into the desired market-sized fruit. The number of the fruit set varies with the prevailing climatic conditions, and the cultural practices employed. Therefore, productivity is not a distinctive characteristic of the new variety.

*Fruit bearing*.—Regular. Fruit set has been more than adequate during the previous years of observation, and thinning was necessary during the past 3 years on both the original seedling and on subsequent asexually reproduced trees.

*Form*.—Upright, and pruned into a central leader shape.

*Density*.—Considered moderately dense. The resulting fruit will color to a commercially acceptable degree with minimal pruning.

TRUNK

*Diameter*.—Approximately 12 cm in diameter when measured at a distance of approximately 15 cm above the soil level. This measurement was taken at the end of the third growing season.

*Bark texture*.—Considered moderately rough, and having numerous folds of papery scarfskin. Since the bark development and coloration change with advancing tree age, this characteristic varies with the tree vigor, age and regional conditions. Therefore, this is not a dependable descriptor of the new variety.

*Lenticels*.—Abundant on new bark. The lenticels are oval in shape, and are approximately 3.0 to 5.5 millimeters in width, and 2.0 millimeters in height.

*Bark coloration*.—Variable, but it is generally considered to be a medium brown, RHS Greyed-Orange Group 165B. This bark coloration was taken from trees in their third leaf. It should be noted that the coloration of the bark is influenced, and varies, as the smoother, darker background color approaches other bark features, and the initial fissures which form a feature of the scarfskin development.

BRANCHES

*Size*.—Considered medium for the variety.

*Diameter*.—Average as compared to other peach varieties. The branches have a diameter of about 4 centimeters when measured during the third year after grafting.

*Surface texture*.—Average.

*Crotch angle*.—Primary branches are considered variable, and are usually growing at an angle of about 50 to about 60 degrees when measured from a horizontal plane. This characteristic can be influenced, to some degree, by tree vigor, rootstock and other cultural conditions.

*Current season shoots*.—Surface texture — Substantially glabrous.

*Internode length*.—Approximately 3.5 cm.

*Color of mature branches*.—Grey brown, RHS Grey-brown Group 199B.

*Current seasons shoots*.—Color — Medium light green, RHS Green Group 144B.

The color of new shoot tips is considered a bright and shiny yellowy-green, RHS Yellow-Green Group N144D. The vegetative shoot color can be significantly influenced by plant nutrition, irrigation practices, and exposure to sunlight, and therefore should not be considered a consistent botanical characteristic of this variety.

LEAVES

*Size*.—Considered medium to large for the species. Leaf measurements have been taken from vigorous, upright current season growth, taken at approximately mid-shoot. It should be understood that the leaf size is often influenced by prevailing growing conditions, quality of sunlight, and the location of the leaf within the tree canopy. For this reason, leaf sizes can vary significantly based upon the ambient and cultural factors listed above, and are not typically considered a dependable botanical descriptor. Leaf bud burst occurs approximately with the first bloom.

*Leaf length*.—Approximately 200-230 millimeters.

*Leaf width*.—Approximately 40-50 millimeters.

*Leaf base-shape*.—The leaves generally exhibit equal marginal symmetry relative to the leaf longitudinal axis.

*Leaf form*.—Lanceolate.

*Leaf tip form*.—Acuminate.

*Leaf color*.—Upper leaf surface, RHS Green Group, 136A.

*Leaf texture*.—Glabrous.

*Leaf color*.—Lower surface, RHS Green Group, 137B.

*Leaf venation*.—Broadly pinnately veined.

*Mid-vein*.—Color — Considered a light yellow-green, RHS Yellow-Green Group, 150A.

*Leaf margins*.—Gently undulating.

*Form*.—Considered bluntly serrate.

*Uniformity*.—Considered generally uniform.

*Leaf petioles*.—Considered canaliculated, that is, having a shallow channel, and more pronounced trough as seen from the dorsal aspect. The petiole margin is considered rounded when viewed from the ventral aspect.

*Size*.—Considered large.

*Length*.—About 15 to 20 mm.

*Diameter*.—About 2.0 to 2.5 mm.

*Color*.—RHS Yellow Green Group, 146B.

*Leaf glands size*.—Considered average for the species, approximately 1 mm in length, and about 1 mm in height.

*Number*.—Generally one to two glands per marginal side are found.

*Type*.—Globose.

*Color*.—RHS Yellow -Green Group 153A.

*Leaf stipules size*.—Medium-large for this variety.

*Number*.—Typically 2 per leaf bud, and up to 6 per shoot tip.

*Form*.—Lanceolate in form, and having a serrated marginal edge.

*Color*.—Green, RHS Green Group, 138A when young, but graduating to a brown color, RHS Greyed-Red Group 182A with advancing senescence. The leaf stipules are generally considered to be early deciduous.

FLOWER BUDS

*Date of first bloom*.—Observed on 30 Jun. 2013.

*Blooming time*.—Considered early in relative comparison to other commercial peach cultivars grown in the same region. The date of full bloom was observed on Jul. 7, 2013. The date of full bloom varies slightly with climatic conditions, and prevailing cultural practices. Flower bud color at pre-bloom and prior to scale separation is green-purple, RHS Greyed-Purple 187C.

*Duration of bloom*.—Approximately 14 days. This characteristic varies slight with the prevailing climatic conditions.

*Flower type*.—The variety is considered to have a showy type flower.

*Flower size*.—Considered medium to large. The flower diameter at full bloom is approximately 40 mm.

*Bloom quantity*.—Considered abundant.

*Flower bud frequency*.—Normally one to two flower buds appear per node.

*Petal size*.—Generally considered medium for the species.

*Length*.—Approximately 15 to 18 mm.

*Width*.—Approximately 12 to 15 mm.

*Petal form*.—Considered an apically rounded ovate.

*Petal count*.—Nearly always 5.

*Petal texture*.—Glabrous.

*Petal color*.—Considered a light pink at the popcorn stage, RHS Red-Purple Group 68A, and darkening with advancing senescence, and the exposure of the petals to sunlight to a medium dark pink, RHS Red-Purple 64C.

*Fragrance*.—Slight.

*Petal claw form*.—The claw is considered ovate, and is generally medium large when compared to other varieties.

*Length*.—Approximately 10 to 13 mm.

*Width*.—Approximately 9 to 11 mm.

*Petal margins*.—Generally considered variable, from nearly smooth to moderately undulate.

*Petal apex*.—Occasionally a small, axially centered groove is noted.

*Flower pedicel length*.—Considered medium long with an approximate length of about 3.5 to 4 mm.

*Diameter*.—Approximately 2 mm.

*Color*.—RHS Grey-Brown 199B.

*Floral nectaries*.—Color: RHS Orange-Red Group 33A.

*Upper portion of the calyx*.—Surface texture — Generally glabrous; Color — RHS Greyed-Purple Group 183C.

*Lower portion of the calyx*.—Surface texture — The surface has a short, fine pubescent texture; Size — Average; Color — RHS Greyed-Red Group 175B.

*Anthers*.—Generally — Average in length.

*Color*.—RHS Greyed-Red Group 181B.

*Pollen production*.—Abundant.

*Color*.—RHS Yellow-Orange Group 21 B.

*Fertility*.—Self fertile.

*Filaments*.—Size — Approximately 12 to 15 mm in length.

*Color*.—RHS Red-Purple Group 65A.

*Pistil*.—Number — usually one, and occasionally more than one.

*Size*.—Average.

*Length*.—Approximately 17 to 19 mm in length including the ovary.

*Color*.—RHS Yellow-Green Group 150C.

FRUIT

*Maturity when described*.—Firm ripe condition (shipping ripe). Date of first picking: Oct. 2, 2013. Date of last picking: Oct. 18, 2013. The date of harvest varies slightly with the prevailing climatic conditions and the current cultural practices.

*Size*.—Generally — Considered medium to large.

*Average cheek diameter*.—Approximately 60 to 68 mm.

*Average axial diameter*.—Approximately 58 to 63 mm.

*Typical weight*.—Approximately 150 grams. This characteristic is quite dependent upon the prevailing cultural practices, and therefore is not particularly distinctive of the new variety.

*Fruit form*.—Generally — Considered slightly oblate. The fruit is generally uniform in symmetry.

*Suture*.—Color — Generally blushed to the same degree as the skin, RHS Red-Purple Group 61B.

*Apex*.—Shape — Rounded.

*Base*.—Generally rounded, and smooth.

*Stem cavity*.—The stem cavity is rounded and uniform in shape. The average depth of the stem cavity is about 10 mm. The average width of the stem cavity is about 15 mm. The average length of the stem cavity when measured in the sutorial plane is about 15 mm.

*Fruit skin*.—Thickness: Considered medium, and tenacious to the flesh.

*Surface texture*.—Short, fine and pubescent. The pubescence is lightly abundant.

*Taste*.—Non-astringent.

*Tendency to crack*.—Not observed in the previous years of observation and evaluation.

*Fruit skin color*.—Blush Color — Generally a Red-Purple blush exists on a preponderance of the skin of the fruit RHS Red-Purple Group 61A. The blush color covers approximately 95% of the fruit skin surface. The percentage of the blush color of the fruit skin can vary, and is generally dependent on the fruit's position in the tree; specific fruit maturity; and also the prevailing ecological, and cultural conditions under which the fruit is grown.

*Ground color*.—Cream, RHS Yellow-White Group 158C. The ground color of the fruit can vary significantly based upon the maturity of the fruit when this measurement is taken.

*Fruit stem*.—Size — Medium in length, approximately 8 to 10 mm.

*Diameter*.—Approximately 2-3 mm.

*Color*.—Pale Yellow-Green RHS Yellow-Green Group 152D.

*Fruit flesh*.—Ripening — Considered even.

*Flesh texture*.—Firm, juicy and dense. Considered non-melting.

*Fibers*.—Numbers — Few.

*Flesh aroma*.—Strong.

*Eating quality*.—Considered very good.

*Flavor*.—Considered well balanced, and having a low acidity.

*Juice production*.—Moderate to high.

*Brix*.—About 10 to 15 degrees. This characteristic varies slightly with the number of fruit per tree; the maturity of fruit when harvested; the prevailing cultural practices; and the ambient climatic conditions.

*Flesh color*.—It is considered a Cream White, RHS White Group 155D.

STONE

*Type*.—Considered clingstone.

*Size*.—Considered small to medium for the variety. The stone varies significantly depending upon tree vigor, the crop load, and the prevailing growing and cultural conditions.

*Length*.—Averaging 25 to 30 millimeters.

*Width*.—Averaging 21 to 25 millimeters.

*Diameter*.—Averaging 18 to 20 millimeters.

*Form*.—Roughly ovoid.

*Stone surface*.—Surface texture: Considered smooth towards the apex, with pitting in the mid section of the stone, and to a lesser extent towards the base.

*Ridges*.—Not overly apparent.

*Ventral edge*.—The ventral edge is considered troughed with two reasonably distinguished edges running parallel to, and on both sides of the stone's suture. These distinct edges continue from the hilum to the apex.

*Dorsal edge*.—Shape — Generally considered smooth.

*Stone color*.—The color of a mature, dry stone is generally considered an orange brown, RHS greyed-orange group 165C. This coloration depends, to some degree, on the moisture content of the stone. This color is variable, however, and may also be affected by oxidation and sun bleaching. This variability in the color which is caused by sun exposure, and the stone's maturity would be considered an inconsistent descriptor of the new variety.

*Tendency to split*.—Splitting has only been rarely noted.

*Kernel*.—Size — Very small.

*Kernel form*.—Uneven.

*Pellicle*.—Slightly pubescent.

*Color*.—RHS Greyed-Orange Group 164B.

*Use*.—The present variety 'Alpine Delight' is considered to be a peach tree of the very early season of maturity, and which further produces fruit which are considered to be very firm, attractively colored, and which are suitable for both local and long distance shipping.

*Keeping quality*.—Excellent. The fruit of this variety have been stored well for periods of up to 30 days after harvest, and at temperatures at or below 1.0 degrees Celsius.

*Shipping quality*.—Good. The fruit of the new variety shows minimal bruising of the flesh or skin after being subjected to normal harvesting and packing procedures. The fruit of the new variety has a non-browning flesh.

*Resistance to insects and disease*.—No particular susceptibilities have been noted. The present variety has not been tested to expose or detect any susceptibilities or resistances to any known plant and/or fruit diseases.

Although the new variety of peach tree possesses the described characteristics when grown under the ecological conditions prevailing near Perth, Australia, it should be understood that variations of the usual magnitude and characteristics incident to changes in growing conditions, fertilization, nutrition, pruning, pest control, frost, climatic variables and changes in horticultural management are to be expected.

Having thus described and illustrated my new variety of peach tree, what I claim is new, and desire to secure by Plant Letters Patent is:

1. A new distinct variety of peach tree, substantially as illustrated and described, and which is characterized principally as to novelty by producing an attractively colored, white fleshed, clingstone peach which is mature for harvesting and shipment approximately October 2 to October 15 under the ecological conditions prevailing near Perth, Western Australia.

* * * * *